(12) United States Patent
Mayenberger et al.

(10) Patent No.: US 6,210,419 B1
(45) Date of Patent: Apr. 3, 2001

(54) SURGICAL CLIP (75) Inventors: Rupert Mayenberger, Rielasingen; Dieter Weisshaupt, Immendingen, both of (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/465,137

(22) Filed: Dec. 16, 1999

(30) Foreign Application Priority Data

Dec. 18, 1998 (DE) .............................................. 198 58 580
Dec. 18, 1998 (DE) .............................................. 198 58 577

(51) Int. Cl.[7] .................................................... A61B 17/04
(52) U.S. Cl. ........................ 606/158; 606/120; 606/151; 606/157
(58) Field of Search ................................... 606/151, 120, 606/157, 158

(56) References Cited

U.S. PATENT DOCUMENTS

| 2,988,314 | * | 6/1961 | Urich ................................ 606/151 |
| 3,616,497 | | 11/1971 | Esposito, Jr. ...................... 24/81 HS |
| 3,629,912 | | 12/1971 | Klopp ................................. 24/255 SL |
| 3,916,908 | | 11/1975 | Leveen . |
| 4,388,747 | | 6/1983 | Plummer .......................... 24/255 SL |
| 4,449,531 | | 5/1984 | Cerwin et al. ...................... 606/157 |
| 4,514,885 | | 5/1985 | Delahousse et al. ................. 24/557 |
| 4,586,503 | | 5/1986 | Kirsch et al. . |
| 4,733,664 | | 3/1988 | Kirsch et al. . |
| 4,929,240 | | 5/1990 | Kirsch et al. ....................... 606/151 |
| 5,032,127 | | 7/1991 | Frazee et al. ....................... 606/143 |
| 5,222,961 | | 6/1993 | Nakao et al. ....................... 606/143 |
| 5,236,440 | | 8/1993 | Hlavacek ........................... 606/219 |
| 5,452,500 | | 9/1995 | Revis . |
| 5,464,413 | | 11/1995 | Siska, Jr. et al. ................... 606/151 |
| 5,625,931 | | 5/1997 | Visser et al. ......................... 24/557 |

FOREIGN PATENT DOCUMENTS

| 30 14 578 | 11/1981 | (DE) . |
| 34 04 561 | 8/1984 | (DE) . |
| 34 43 367 | 6/1985 | (DE) . |

OTHER PUBLICATIONS

*Patent Abstracts of Japan*, Abstract of Japanese Patent No. 6–233774, "Tissue Ligator", vol. 18, No. 610, Nov. 21, 1994.

* cited by examiner

*Primary Examiner*—Gary Jackson
(74) *Attorney, Agent, or Firm*—Barry R. Lipsitz (57) ABSTRACT

A U-shaped surgical clip having two arms is provided. The arms are connected to one another via a deformable web. In order firstly to increase the application safety and secondly to simplify application, it is proposed that, via the junction point of the arms with the web, the arms comprise rearwardly projecting extensions. Interacting catches are disposed at these extensions and/or at the deformable web. The catches fix the extensions to one another and/or fix the web to these extensions when the web is deformed upon the compression of the arms and is forced against the extensions.

22 Claims, 6 Drawing Sheets

SURGICAL CLIP

This application is related to co-pending application Ser. No. 09/458,290 filed Dec. 10, 1999.

BACKGROUND OF THE INVENTION

The present invention relates to a U-shaped surgical clip having two arms that are connected to one another via a deformable web.

Such surgical clips are used to clamp vessels. In the case of known surgical clips, the arms, which on the inside are constructed as clamping jaws, are laid against both sides of a vessel and are compressed, deforming the clip. Thus the webs firstly have to be easily deformable for the application of the clips. Secondly, in the case of conventional clips, they have to absorb the clamping forces. In order to remain in this clamping position, the web connecting the arms has to have a very strong construction, since it has to retain the already assumed position after deformation. As a result, different demands on the webs are produced, which are to some extent difficult to meet. In many cases the strength of a clip whose arms are held together just by the web is not sufficient.

SUMMARY OF THE INVENTION

The object of the invention is to develop a generic surgical clip so that on the one hand it can be easily deformed upon application, whereas on the other hand it produces high retention forces in the applied state.

This object is achieved in accordance with the invention with a surgical clip of the type described at the beginning in that, via the junction point of the arms with the web, the arms comprise rearwardly projecting extensions and in that disposed at these extensions and/or at the deformable web are interacting catch means, which fix the extensions to one another and/or to the web that is deformed during the compression of the arms and is forced against the extension. As a result, the arms are securely retained in the clamping position.

In a preferred exemplified embodiment, it is specified that the interacting catch means is disposed along the extensions and along the deformable web, such that upon compression of the clip the web is deformed and forced against the extensions thereby fixing the web to the extensions.

As a result, it is ensured that the holding together of the arms that have been brought closer together has been achieved not just by the web, but also by the catch means.

By this fixing of the deformed arms at the extensions, a large part of the length of the webs is securely connected by these catch means to the arms, so that in this manner considerable retention forces can be exerted on the closed clip, even if the web itself has an easily deformable and accordingly flexible construction.

The catch means securing the deformed web to the extensions may be projections or recesses that engage in one another, in particular by friction or by positive locking.

It is favorable if the catch means comprise elastically deformable undercuts, which engage with one another upon the dipping of the projections into the recesses. As a result, a permanent fixing of the portions of the webs that are applied to the extensions is ensured, and thus the possibility of the arms moving away from one another in the region of the webs fixed in this manner is safely avoided.

In a preferred exemplified embodiment, it is specified that the projections have a ledge-shaped construction and the recesses have a groove-shaped construction. Ledge-shaped projections, which are disposed for example on the outside of the web, then result in the web being reinforced over the length of the projections. Flexibility then occurs only in the region between the ledge-shaped projections, and in this region the web can be constructed in the manner of an integral hinge joint.

In a preferred embodiment, it is specified that at least one catch projection is disposed at the web as catch means on either side of its center. In this case, it is favorable if the web comprises a flexible central portion in the region between the two central projections.

With such a configuration, in accordance with another preferred embodiment it can be specified that next to the flexible central portion there is at least one secondary web, the end of which is connected to the web or to the adjacent projections. Such a secondary web stabilizes the web in the region of the flexible central portion, so that before the deformation this flexible central portion is reinforced. The two arms are therefore kept by the web at a fixed distance, and this is favorable when the clips are to be inserted into a magazine in a manner known per se and are to be guided therein, in which case the guidance occurs by placing the arms against external guides.

In another preferred embodiment, it is specified that the web comprises a lug on its outside which on each opposite side bears at least one catch means. In this case the web remains flexibly constructed over its entire length, and the catch means are borne by the lug which connects the webs with the extensions of the arms when the clip is compressed. In this configuration, it is also favorable if the lug or the catch means disposed thereon are connected via a secondary web with regions of the web lying closer to the arms, and thereby a stabilization and reinforcement of the web is also produced before the compression of the clip.

It is particularly favorable if these secondary webs have a weaker construction than the web itself, so that the secondary webs break upon the bending together of the web. As a result, stabilization is produced only during the non-deformed initial state of the clip. As soon as the clip is deformed by bringing the two arms closer together, the secondary webs break and the web becomes flexible until the clip is completely compressed and the two arms are fixed in relation to one another by the locking of the flexible web with the extensions.

It is favorable if the web is constructed as a flexible strip at least in its central portion.

In another preferred embodiment, it is specified that the extensions bear further catch means which upon the compression of the arms fix the extensions themselves to one another. Thus, not only the web sections are fixed on the extension, but by further catch means the two extensions are also directly connected with one another in the deformed state of the clip. In this case it is favorable if the catch means fixing the extensions to one another are disposed at the rear end of the extensions, and thus there remains a sufficient length of the arms for the fixing of the web sections between the junction of the web into the arms on the one hand and these further catch means on the other hand.

In another preferred embodiment, it is specified that only the extensions bear catch means disposed at the rear end of the extensions, which upon the compression of the arms fix the extensions themselves to one another. Furthermore, it may be specified that at the front end of the clip the arms bear catch means, which upon the compression of the arms fix the arms to one another. Thus, an annular enclosure of the vessel surrounded by the clip occurs, and in particular in the case of clips which bear such catch means both at the front and also at the rear end, the arms can be permanently connected to one another at both ends, in which case the web portions may be additionally connected to the arms so that a particularly strong and secure holding together of the arms in the clamping position is guaranteed.

The clip is preferably made from plastics material, in particular from reabsorbable plastics material.

It is favorable if both arms are outwardly curved and the convex sides are faced towards one another. As a result, the central regions are outwardly curved upon the application of the clip and receive a tensile force. This effect is reinforced if, in accordance with another preferred embodiment, the arms have a smaller cross section in the central region than in the front region and than in the rear region. As a result, a very uniform clamping of the vessel enclosed between the arms is produced.

The following description of preferred embodiments of the invention serves for further explanation in conjunction with the drawings.

DETAILED DESCRIPTION OF THE INVENTION

Figure 1:
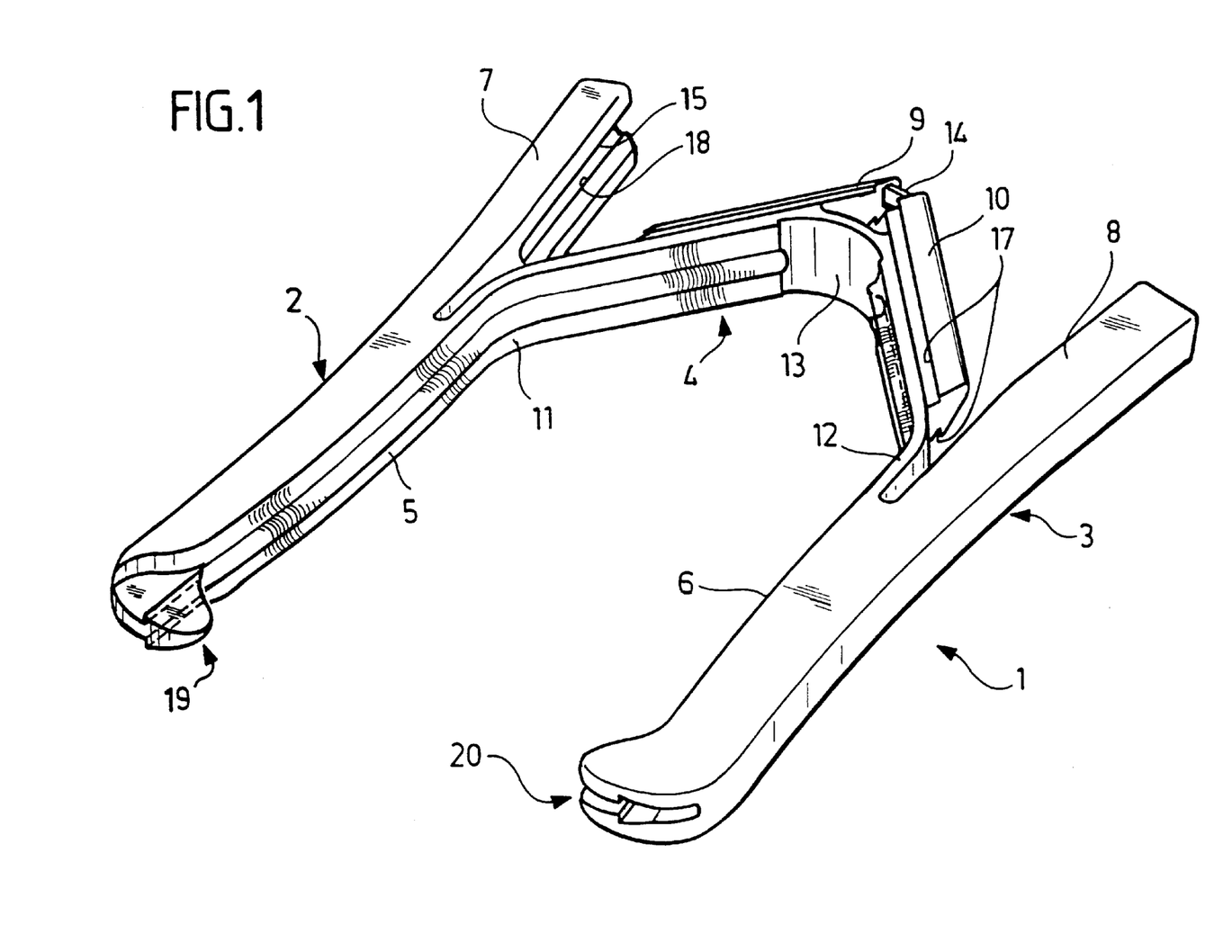
FIG. 1 shows a perspective view of a first preferred exemplified embodiment of a clip in the non-deformed state.
Figure 2:
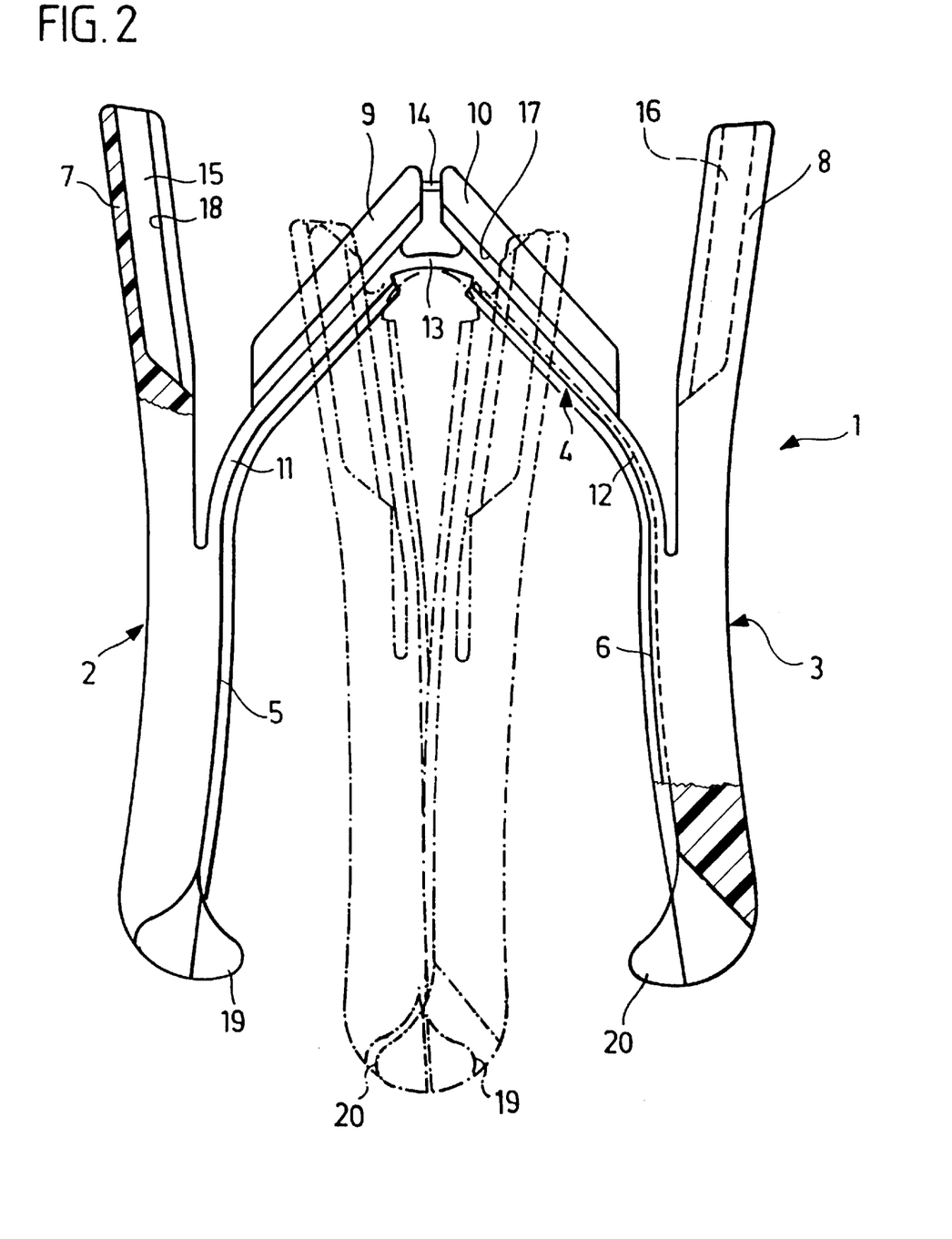
FIG. 2 shows a top view of the clip of FIG. 1 in the non-deformed state (unbroken lines) and in the closed state (dot-dash lines)

The clip 1 represented in FIGS. 1 and 2 comprises two arms 2, 3 which extend substantially parallel to one another and which have a substantially rectilinear construction with a slight outward curvature so that the convex inner sides of these arms 2 and 3 are faced towards one another.

In the central region both arms 2, 3 have a cross section that is reduced in relation to the front and rear end, and in this central region both arms 2, 3 are connected to one another via a strip-shaped, flexile web 4.

The inner sides of the two arms 2, 3 form, between the front end and the junction of the web 4, clamping jaws 5, 6, which may be contoured in a suitable manner known per se, and in each case the section of the arms 2, 3 between the rear end and the junction of the webs 4 forms an extension 7, 8.

The web 4 bears on its outer side, spaced from one another and symmetrically to its center, two ledge-shaped projections 9, 10, which strengthen the web 4 over its length and in this manner define three hinge-joint regions, namely a hinge-joint region 11 at the junction of the web 4 into the arm 2, a hinge-joint region 12 at the junction of the web 4 into the arm 3 and a central hinge-joint region 13 between the two projections 9 and 10.

The two projections 9 and 10 are connected to one another via a secondary web 14, which extends parallel to the central hinge-joint region 13 spaced from the web 4 and which stabilizes the web 4 in the central hinge-joint region 13. As a result, the two projections 9 and 10 and the portions of the web 4 associated with them enclose a fixed angle with one another when the clip is undeformed, for example an angle of roughly 90°. The strength of the secondary web 14 is chosen so that upon the bending together of the web by deformation of the central hinge-joint region 13 the secondary web 14 breaks open and thus easily permits a deformation of the central hinge joint-region 13.

Situated in the two extensions 7 and 8 are longitudinal grooves 15, 16 that are open to the inside and which are disposed and dimensioned so that, upon the compression of the two arms 2 and 3 and the resultant folding together of the sections of the web 4, the projections 9 and 10 dip into the longitudinal grooves 15 and 16. In this inserted position, the projections 9 and 10 are retained in the longitudinal groves 15 and 16 either frictionally by clamping or by positive locking. In the represented exemplified embodiment, the projections 9 and 10 comprise lateral catch projections 17, which engage behind corresponding catch projections 18 in the longitudinal grooves 15, 16. The catch projections 17 and 18 are elastically deformable, so that upon the entry of the projections 9 and 10 into the longitudinal grooves 15 and 16 they yield and enable the entry, but the projections 9 and 10 are prevented from moving out of the longitudinal groves 15 and 16 by the catch projections 17 and 18.

The clip represented in FIGS. 1 and 2 is made from plastics material, in particular from a reabsorbable plastics material, and is preferably constructed as a single-part component.

To apply this clip, the clip is, for example, displaced in a magazine in which the arms 2 and 3 abut guides with their outer sides. This position is stabilized by the central hinge-joint region 13 of the web 4 being firstly strengthened by the secondary web 14, as a result of which perfect guidance in the magazine is guaranteed without the danger of jamming.

For the application itself, the arms 2 and 3 of the opened clip 1 are moved up on either side to a vessel to be clamped, and then the two arms 2 and 3 are guided towards one another by a suitable tool, so that the clamping jaws 5 and 6 clamp the vessel enclosed between them in the desired manner.

In so doing, the secondary web 14 breaks open, the web 4 is deformed until the web sections lie against the inner side of the extensions 7 and 8, and in this position the web is stabilized by the dipping of the projections 9 and 10 into the longitudinal grooves 15 and 16, i.e. in the rear part of the clip it is no longer possible to distance the arms 2 and 3 from one another.

Projections 19, 20 are provided that are directed towards one another and that are constructed as catch projections. These are represented in the front region in the exemplified embodiment of FIGS. 1 and 2, so that when the arms 2 and 3 are brought closer to one another they are also locked with one another in the front region, with the result that there, also, it is no longer possible to distance the arms 2 and 3 from one another.

Figure 4:
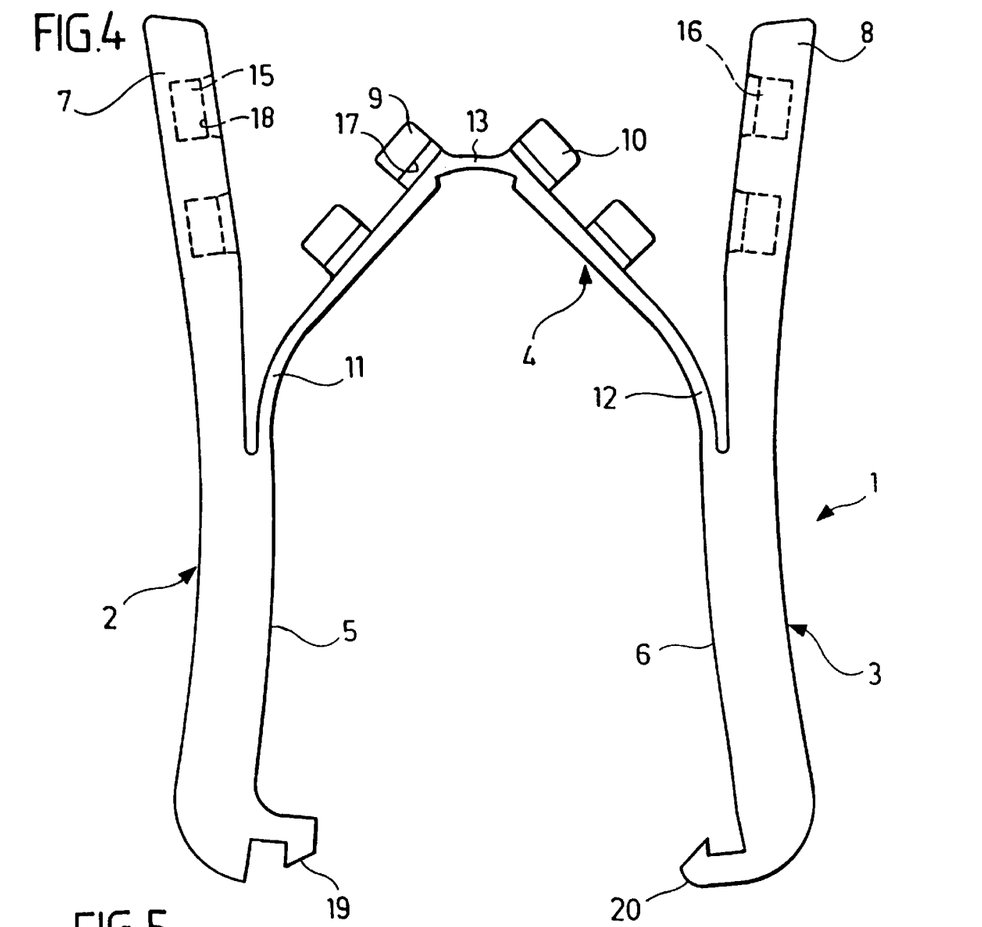
FIG. 4 shows a view similar to FIG. 2 in the case of another modified exemplified embodiment of a clip with an additional catch on the front end of the clamping jaws.
Figure 5:
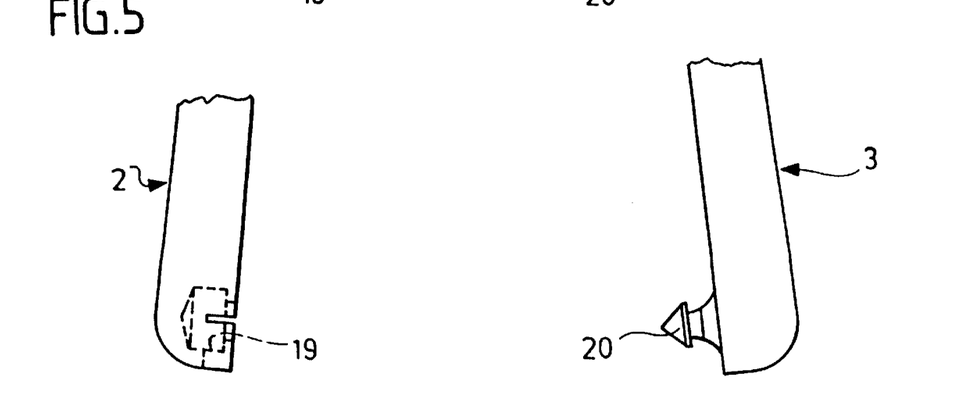
FIG. 5 shows an alternative solution for a locking of the arms of the clip at the front end of the clamping jaws.

Such projections 19 and 20, which are constructed as catch projections, are for example also represented in the exemplified embodiments of FIGS. 4 and 5, and in this case it involves catch projections with undercuts which in the closed state engage behind one another.

Figure 3:
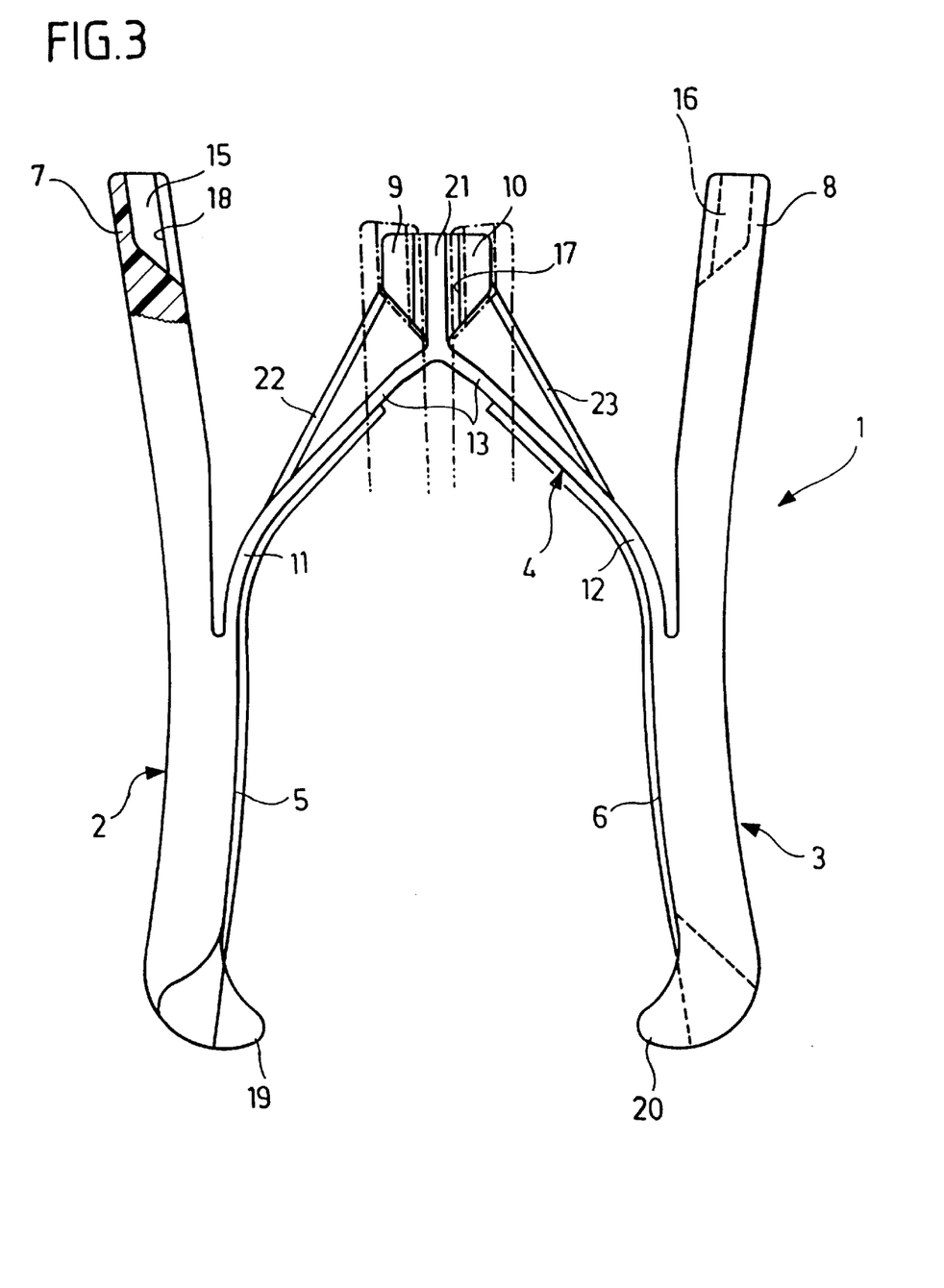
FIG. 3 shows a view similar to FIG. 2 in the case of a modified exemplified embodiment of a clip.

Represented in FIG. 3 is a modified exemplified embodiment of a clip, which has a very similar design to the clip in FIGS. 1 and 2, and therefore identical parts have the same reference numbers. In contrast to the clip in FIGS. 1 and 2, the projections 9 and 10 in this exemplified embodiment are not placed directly on the outside of the web, but these projections 9 and 10 are integrally formed on a lateral lug 21, which in the center of the web 4 protrudes from said web. All remaining regions of the web 4 are constructed as flexible strip material, however these regions are stabilized by secondary webs 22 and 23, which connect the projections 9 and 10 each with a part of the web 4 that is remotely situated. Here too, the secondary webs 22 and 23 have a weaker construction than the web 4 itself, so that upon the compression of the clip the secondary webs 22 and 23 break open and enable a free deformation of the web 4.

As in the exemplified embodiment of FIGS. 1 and 2, the projections 9 and 10 dip into the longitudinal grooves 15 and 16 when the clip is compressed.

The clip in FIG. 4 has a similar design, so that parts corresponding to one another bear the same reference numbers. In this exemplified embodiment, several projections 9, 10, which dip into a number of corresponding longitudinal grooves 15, 16 of finite length, are disposed on the outside of the web 4. In this exemplified embodiment no secondary web 14 is represented, however it could also be easily used in this exemplified embodiment.

As already mentioned, the exemplified embodiment of FIG. 4 shows projections 19 and 20 constructed as hook-shaped catch elements, which connect the arms 2 and 3 with one another at their front end when the clip is compressed. Catch projections constructed in this manner can be used in all clip designs, and the same applies with respect to the modified exemplified embodiment of FIG. 5. In FIG. 5, the catch elements 19 and 20 have a similar construction to the catch recess 24 and catch projection 25 described in the exemplified embodiment of FIG. 6 at the rear end of the extensions 7, 8.

Figure 6:
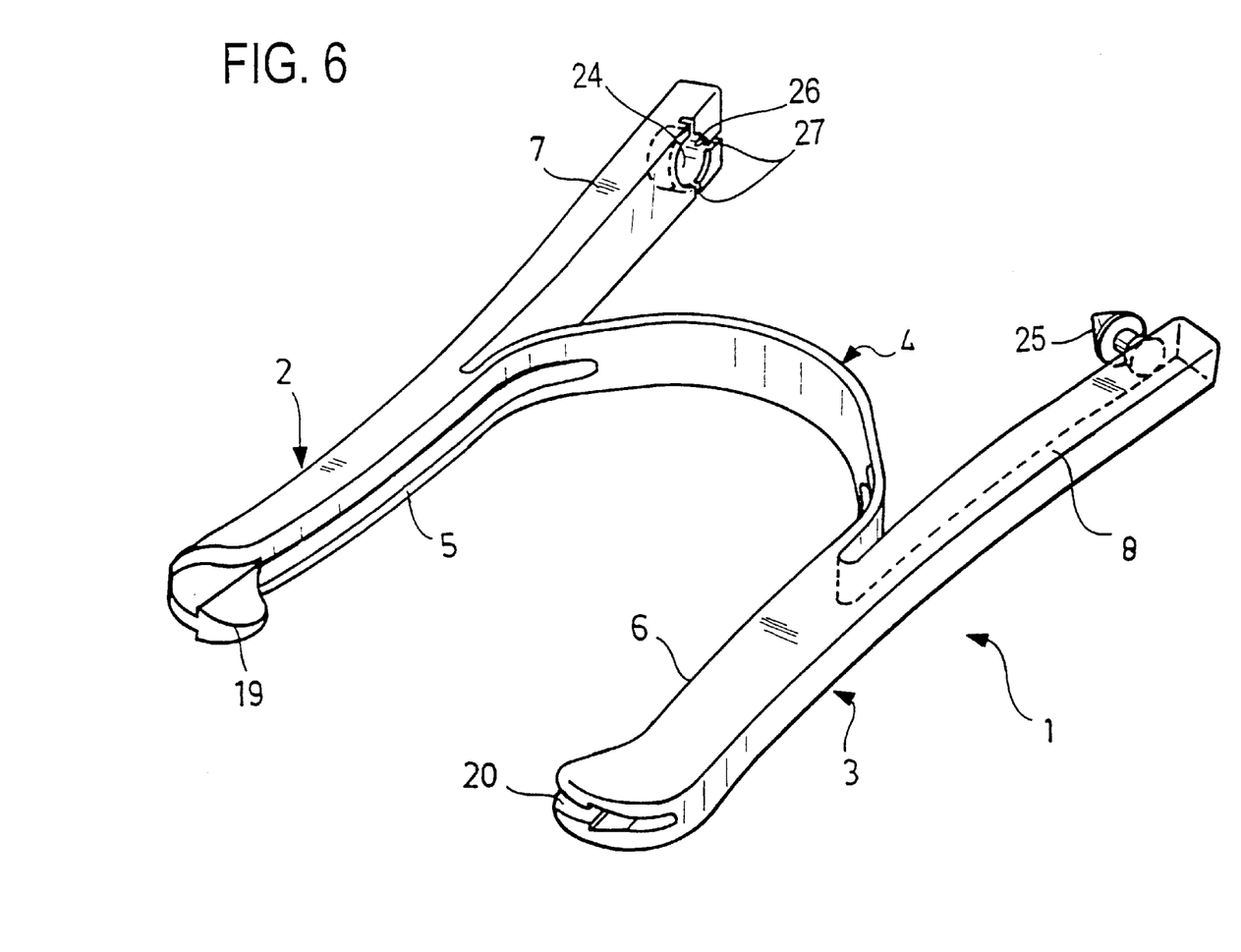
FIG. 6 shows a view similar to FIG. 1 with a clip having catch means at the rear end of the extensions.

The clip represented in FIG. 6 is limited in its representation to the two arms 2 and 3 and the web 4, but it is obvious that the remaining configurations of the described exemplified embodiments can be used with this clip too.

In addition to the already described catch means, in this exemplified embodiment catch recesses 24 and catch projections 25 that interact are also provided at the rear end of the arms 2 and 3, i.e. at the rear end of the extensions 7 and 8, which catch means fixes the arms 2 and 3 directly to one another also at the rear end when the clip is compressed.

Figure 7:
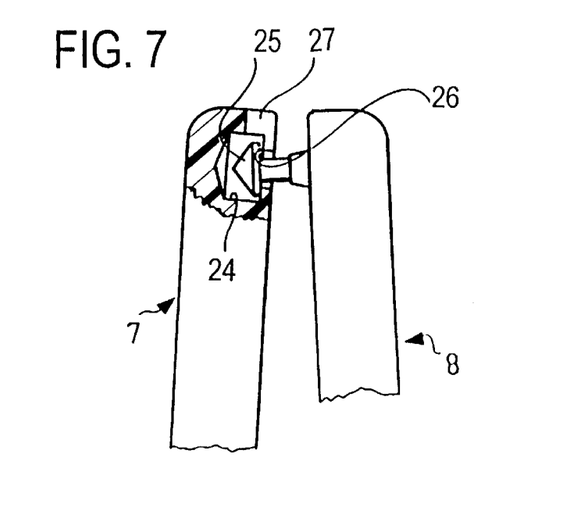
FIG. 7 shows a detailed view of the rear end of the extensions in the case of the clip of FIG. 6 in the brought-together state.

The catch recess 24 and catch projection 25 are arranged and dimensioned so that upon the compression of the clip 1 with the deformation of the strip-shaped web 4 the projection 25 dips into the recess 24. In so doing, the projection 25 elastically expands the recess 24, which for this purpose has a notch 27 from the rear end of the extension 7. The edge of the recess 24 on the entry side forms a slightly protruding catch projection 26, behind which the projection 25 locks, so that the projection 25 can no longer be withdrawn from the recess 24 (FIG. 7). As a result, the two extensions 7 and 8 are fixed to one another in the region of their rear end.

In the exemplified embodiment of FIG. 6, the arms 2 and 3 are provided in the front region, i.e. at the front end of the clamping jaws 5, 6, with catch projections 19, 20, which upon the bringing together of the arms 2 and 3 engage in one another and consequently fix the arms 2 and 3 to one another at the front end as well.

Such a locking of the extensions 7 and 8 and the locking of the projections 19 and 20 produces a clip which in the applied state clamps an enclosed vessel in a permanent and strong manner without there being the danger of this clip unintentionally opening. Here the retaining forces are not produced by bending resistance of the web 4, so that the web 4 itself may have a flexible and easily deformable construction, facilitating the application of the clip 1.

Figure 8:
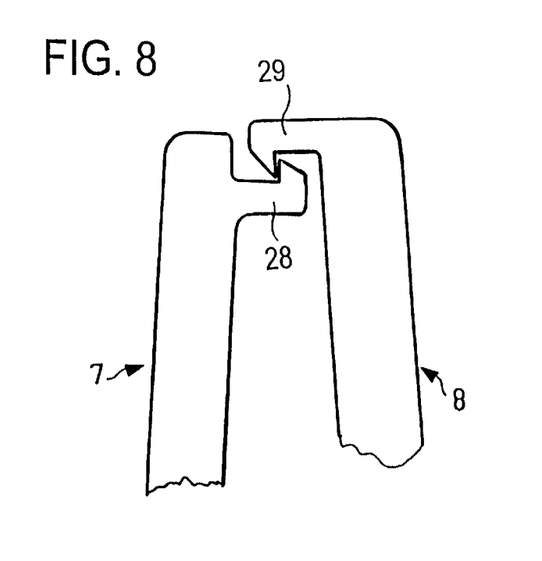
FIG. 8 shows a view similar to FIG. 7 with a modified configuration of the catch means.
Figure 9:
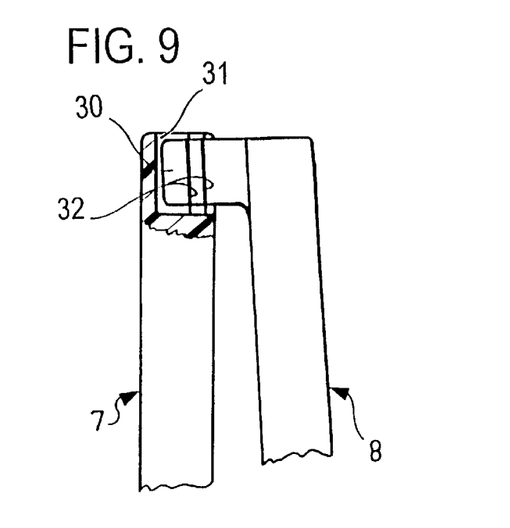
FIG. 9 shows a view similar to FIG. 7 with a modified configuration of the catch means.
Figure 10:
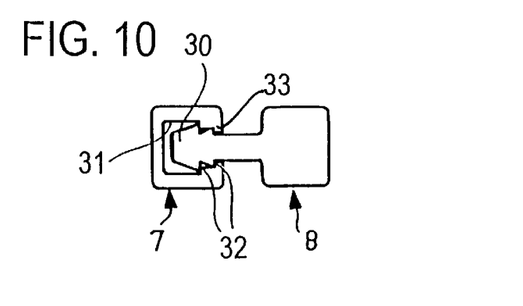
FIG. 10 shows a top view of the rear end of the extensions represented in FIG. 9.

The configuration of the recess 24 and of the projection 25 can be modified. For example, in FIG. 8 two hook-shaped catch elements 28 and 29 are shown, which fix the extensions 7 and 8 to one another. In the exemplified embodiment of FIG. 9, a ledge-shaped projection 30 engages in a groove-shaped recess 31. The projection 30 laterally bears several catch shoulders 32, which engage behind a catch projection 33 of the recess 31 and thus enable a fixing of the projection 30 in the recess 31 to different depths (FIG. 10).

In particular the catch means of the two arms at the rear end and at the front end combined with the curved shape of the arms 2 and 3 and the weakening of the cross section in the central part of the arms 2 and 3 results in the clamped vessel being retained over the entire length of the clamping jaws in a uniform, strong and especially secure manner.

What is claimed is:

1. A U-shaped surgical clip comprising:
   two arms that are connected to one another via a deformable web, wherein, via the junction point of the arms with the web, the arms comprise rearwardly projecting extensions; and
   catch means disposed at the extensions and at the deformable web, said catch means being operable to fix the web to the extensions when the web is deformed upon the compression of the arms and forced against the extensions, wherein,
   the two arms are fixed in a clamped state upon compression of the arms.

2. A surgical clip according to claim 1, wherein the catch means are projections and recesses that engage with one another with positive locking.

3. A surgical clip according to claim 2, wherein the catch means comprise elastically deformable undercuts which engage behind one another upon the dipping of the projections into the recesses.

4. A surgical clip according to claim 1, wherein the catch means are projections and recesses that frictionally engage with one another.

5. A surgical clip according to claim 4, wherein the projections have a ledge-shaped construction and the recesses have a groove-shaped construction.

6. A surgical clip according to claim 4, wherein at least one catch projection is disposed at the web as catch means on either side of its center.

7. A surgical clip according to claim 6, wherein the web comprises a flexible central section in the region between two central projections.

8. A surgical clip according to claim 7, wherein next to the flexible central section there is at least one secondary web, the end of which is connected to the web or the adjacent projections.

9. A surgical clip according to claim 8, wherein the secondary webs have a weaker construction than the web itself, so that the secondary webs break when the web bends.

10. A surgical clip according to claim 6, wherein in its center the web has a lug on the outside, which on each opposite side bears at least one catch means.

11. A surgical clip according to claim 10, wherein the lug or the catch means disposed thereon are connected via secondary webs to regions of the web that are closer to the arms.

12. A surgical clip according to claim 1, wherein the web is constructed as a flexible strip at least in its central portion.

13. A surgical clip according to claim 1, wherein the extensions bear further catch means which upon the compression of the arms fix the extensions themselves to one another.

14. A surgical clip according to claim 13, wherein the further catch means fixing the extensions to one another are disposed at the rear end of the extensions.

15. A surgical clip according to claim 1, wherein the catch means fixing the extensions to one another are disposed at the rear end of the extensions.

16. A surgical clip according to claim 1, wherein at the front end of the clip the arms bear catch means which upon the compression of the arms fix the arms to one another.

17. A surgical clip according to claim 1, wherein the clip comprises a plastic material.

18. A surgical clip according to claim 17, wherein the plastic material is reabsorbable.

19. A surgical clip according to claim 1, wherein both arms are outwardly curved and the convex sides are faced towards one another.

20. A surgical clip according to claim 1, wherein the arms have a smaller cross section in a central region than in a front region and than in a rear region.

21. A U-shaped surgical clip having two arms that are connected to one another via a deformable web, wherein:

- at the junction point of the arms with the web, the arms comprise rearwardly projecting extensions that bear first catch means which fix the two arms in a clamped state upon compression of the arms; and
- at the front end of the clip the arms bear second catch means which fix the two arms to one another in a clamped state upon compression of the arms.

22. A U-shaped surgical clip having two arms that are connected to one another via a deformable web, wherein:

- at the junction point of the arms with the web, the arms comprise rearwardly projecting extensions that bear catch means which fix the two arms in a clamped state upon compression of the arms; and
- the arms have a smaller cross section in a central region than in a front region and than in a rear region.

* * * * *